(12) United States Patent
Dubey et al.

(10) Patent No.: US 8,318,216 B2
(45) Date of Patent: Nov. 27, 2012

(54) AYURVEDIC FORMULATION ADVOCATED FOR THE PREVENTION AND MANAGEMENT OF CORONARY HEART DISEASE

(75) Inventors: Govind Prasad Dubey, Uttar Pradesh (IN); G. Victor Rajamanickman, Kerala (IN)

(73) Assignee: Anurag Sharma, Kolkata (IN)

( * ) Notice: Subject to any disclaimer, the term of this patent is extended or adjusted under 35 U.S.C. 154(b) by 98 days.

(21) Appl. No.: 12/866,389

(22) PCT Filed: Jun. 5, 2009

(86) PCT No.: PCT/IN2009/000324
§ 371 (c)(1),
(2), (4) Date: Feb. 23, 2011

(87) PCT Pub. No.: WO2010/100652
PCT Pub. Date: Sep. 10, 2010

(65) Prior Publication Data
US 2011/0135771 A1  Jun. 9, 2011

(30) Foreign Application Priority Data

Feb. 4, 2009  (IN) .................................. 196/KOL/09

(51) Int. Cl.
*A01N 65/00*  (2009.01)
(52) U.S. Cl. ...................................................... 424/725
(58) Field of Classification Search .................. None
See application file for complete search history.

(56) References Cited

FOREIGN PATENT DOCUMENTS

WO  0190064 A2  11/2001
WO  2005016361 A1  2/2005

*Primary Examiner* — Michael Meller
(74) *Attorney, Agent, or Firm* — The Webb Law Firm

(57) ABSTRACT

A novel herbal formulation for the prevention and management of various CHD risk factors including vascular inflammatory process responsible for cardiovascular events comprising a hydro-alcoholic extraction of *Commiphora mukul*, *Terminalia arjuna*, *Inula recemosa* and *Hippophae rhamonoides* with or without known additives.

6 Claims, No Drawings

AYURVEDIC FORMULATION ADVOCATED FOR THE PREVENTION AND MANAGEMENT OF CORONARY HEART DISEASE

FIELD OF INVENTION

The present invention relates to the novel herbal formulation and to the process thereof for the prevention and management of a plurality of risk factors responsible for cardiovascular disorders. The preparation of present invention may be advantageously used for the prevention and management of dyslipidemia, obesity, hypertension, glucose intolerance, hyperthomocysteinemia, vascular inflammation along with anxiety and stress.

BACKGROUND OF INVENTION

Coronary heart diseases (CHD) represents an insidious process that starts in early life and progresses steadily throughout the years until manifested by one or more conditions. Essential hypertension is one of the major risk factors for the occurrence of CHD. The conventional risk factors like dyslipidemia, obesity, diabetes mellitus, anxiety and stress are responsible for hypertension and cardiovascular disorders. Unless the risk factors associated with CHD are managed. It is not possible to prevent the incidence of CHD.

The prevention and management of coronary risk factors includes prevention of occurrence of CHD risk factors before clinical manifestation of CHD and management of coronary risk factors after clinical manifestation. Several studies are in support that by managing the hypertension and reducing the lipid levels the incidence of CHD can be minimized.

There is ample evidence to prove that hypercholesterolemia and hypertriglyceridemia have positive correlation with atherosclerosis, CHD and stoke. It has been observed that consumption of starch is prone to develop cardiovascular disorders due to atherogenic injury than the consuming less starch. In long course of time this alters the genetic character, rendering people with such consumption more susceptible to develop early atherosclerosis, hypertension and hyperlipidemia. Elevated serum cholesterol, LDL-c and low HDL-c are major independent conventional risk factor CHD and atherosclerotic event. High concentration of triglycerides, small dense LDL-c and low level of HDL-c is referred to as dyslipidemic and this process is responsible for insulin resistance. Insulin resistance syndrome is characterized by a number of cardiovascular risk factor like central obesity, hyperglycemia, hypertension, dyslipidemia along with pro-coagulant factors and inflammatory markers. Studies have demonstrated a significant reduction in CHD events among diabetic cases by the proper management of hypercholesterolemia.

Recent task factors inflammation and acute phase reactants circulating cytokines, hs C-reactive protein (CRP), serum albumin and fibrinogen are predictor of onset of CHD and recurrent acute myocardial infarction. Several studies have shown that elevated homocysteine (Hcy) is frequent in persons with CVD and it is strong and independent risk factors for adverse cardiac events.

Elevation of Hcy is associated with an increased risk of cardiovascular disease and the cause is deficiency of folate. One of the experimental studies reported that hyperhomocysteinemia evoked by folate depletion increases arterial permeability and stiffness. The address effect of elevated hcy level involve oxidative damage to vascular endothelial cells, increased proliferation of smooth muscle cells and high oxidized LDL-c leading to atherosclerosis. Thus, it is responsible for endothelial dysfunction. Similarly increased CRP has a major role in the pathogenesis of atherosclerosis. CRP and other inflammatory sensitive proteins are primarily related to changes in plaque morphology and possibility to rupture and acute thrombosis.

Elevated levels of circulating cytokines have been demonstrated in patients with heart failure. IL-6 concentration was related to severity of left ventricular dysfunction and to the degree of activation of the sympathetic and rennin-angiotensin systems. Thus cytokines including IL-1, IL-6 and TNF-α are responsible for the development of progression of coronary heart diseases. IL-6 is genetically determined and level determines the risk of atherosclerosis, thrombosis and CHD.

Adiponectin, is also inversely related to blood pressure, heart rate, total cholesterol, LDL-c, and triglycerides and positively related with HDL-c. It is proposed that CRP, fibrinogen, lipoprotein (a) and homocysteine are important bio-markers for assessment of CHD risk even in asymptomatic individuals with strong family history of conventional risk factors of CHD.

Recently some of the biomarkers are emerging useful in the diagnosis and treatment of the pathophysiology of cardiac disease like cardiac troponin (cTn), β-type natriuretic peptide (BNP) is a 32-amino-acid counter regulatory peptide release in response to cardiac stretch. BNP values have shown strong correlation with age and acute coronary syndrome cases. Elevated BNP is responsible for stroke, obstructive sleep apnea, diabetes, left ventribular hypertrophy and stable CAD. 3CD40 legand a signaling protein was found to be significantly elevated with acute coronary syndrome.

Psychosocial stress also plays an important role in the precipitation of arterial hypertension, angina pectoris and myocardial infarction. Depression is an independent risk factor for development of CHD. Thus stress management contribute in the prevention of adverse cardiac event. Reduction in obesity index is also helpful in reducing the incidence of CHD.

Many synthetic conventional drug therapy are used such as anti-hypertensive, anti-arrhythmic, hypolipidaemic, anti-diabetic, anti-obesity, agents but their application are limited are prolonged use can produce untoward effects on biological system.

OBJECTS OF THE INVENTION

The primary object of the present invention is to propose a plant based formulation beneficial in the prevention and management of various CHD risk factors with the view of prevent/minimize the adverse cardiac event.

Another object of the present invention is to propose a herbal formulation having beneficial role in the prevention and management of abnormal lipids, particularly reducing the total cholesterol and LDL-cholesterol so that atherosclerotic process can be checked.

Still another object is to propose a plant based formulation for the prevention and management of high level of triglycerides responsible for ahterogenic injury.

Still another object of the present invention is to propose a herbal formulation having that may advantageously in the management of hypertension which is the most important risk factor of cardiovascular disorder.

Yet another object of the present invention is to propose a herbal formulation beneficial in the prevention and management of high Body Mass Index as obesity is one of the most important risk factors for CHD.

Further object of this invention is to propose a herbal formulation showing alpha-glucosidase inhibiting property and effective in the management of abnormal glucose metabolism and reducing the insulin load and post Glycemic index.

One of the objects of the present invention is to propose a herbal formulation effective in the management of elevated homocysteine level as it is an independent risk factor for CHD.

Another object of the present invention is to propose a herbal formulation having beneficial effect on pro-inflammatory bio-markers hs CRP, TNF-α and Interleukin-6, and thus reducing the vascular complications before and after onset of adverse cardiac event.

Still another object of the present invention is to propose a herbal formulation beneficial in reducing the endotheline a bio-marker for endothelial dysfunction associated with various CHD risk factors.

Further object of the present invention is to propose a herbal formulation effective in regulating the adipocytokines particularly leptin and adiponectin involved in atherosclerotic process.

Object of this invention is to propose a herbal formulation effective in the prevention and management of anxiety and depression associated with CHD.

SUMMARY OF THE INVENTION

According to this invention there is provided a novel herbal formulation showing in the prevention and management of various CHD risk factors including vascular inflammatory process responsible for cardiovascular events comprising a hydro-alcoholic extraction of *Commiphora mukul, Terminalia arjuna, Inula recemosa* and *Hippophae rhamonoides* with or without known additives.

Further according to this invention there is provided a process for preparation of novel formulation comprising of the steps preparing hydro-alcoholic extract of *Commiphora mukul, Terminalia arjuna, Inula recemosa* and *Hippophae rhamonoides* by using water (aqueous) and methanol at 70-80° C. and maintaining the pH of solution between 7-10 separating chromotographically the active compound by using TLC, HPLC and HPTLC, supporting with molecular characterization of the plant extract by using IR and NMR. Water (aqueous) and methanol may preferably be 70:30 present in the ratio for the prevention and management of various CHD risk factors.

DETAILED DESCRIPTION OF THE INVENTION

The hydro-alcoholic extract of four Ayurvedic plants comprising mukul, *Terminalia arjuna, Inula recemosa* and *Hippophae rhammnoides* was prepared by using 30:70 ratio of water (aqueous) and methanol. The water utilized for extraction was decontaminated for any type of bacterial or abnormal growth by using reverse osmosis plant. After extraction the active molecules was identified and separated by HPLC, HPTLC and NMR procedure.

The biological activity was studied on the bases of mode of action of the test drug and effect on various parameters undertaken for this clinical condition. The molecular characterization was done by using NMR and bio-molecular markers responsibly for dyslipidemia, atherosclerotic changes, obesity, dyslipemia, hyperglycemia, hyperhomocysteinemia, hyperleptinemia, low adiponectin level including vascular inflammatory process.

The pre-clinical toxicological studies were carried out to determine the safety and efficacy profile of individual as well as combined test formulation before going for human use. The mode of action of single and combined formulation was carried out in animal models.

The anti-inflammatory, anti-obesity, anti-atherogenic, anti-oxidant, leptic reducing and adiponectin enhancing property of test formulation was established in animal model before using the drug for human consumption.

Extraction Procedure

Process for extraction of test formulation containing gum resin of *Commuphora mukul*, bark of *Terminalia arjuna*, root of *Inula recemosa* and leaves and fruits of *Hippophae rhammoides*.

The hydro-alcoholic extract (30:70) were utilized for the extraction of active compound found in plants. After extraction of the plants the chromatography separation were carried out by using TLC, HPLC and HPTLC. After identification and separation of the active compound, the molecular characterization was carried out by using IP and NMR. The photo-estrogen were separated and identification of ratio between the active molecule and the extract were determined.

The extraction was done at the temperature of 70-80° C. The pH of the solution was maintained between 7-10. The following steps were carried out to separate the active compounds.

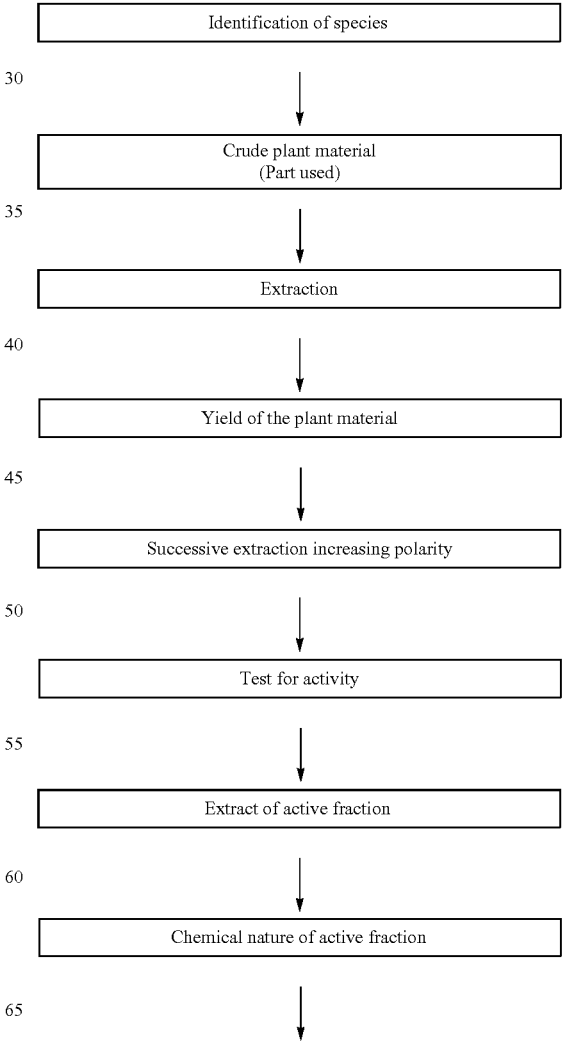

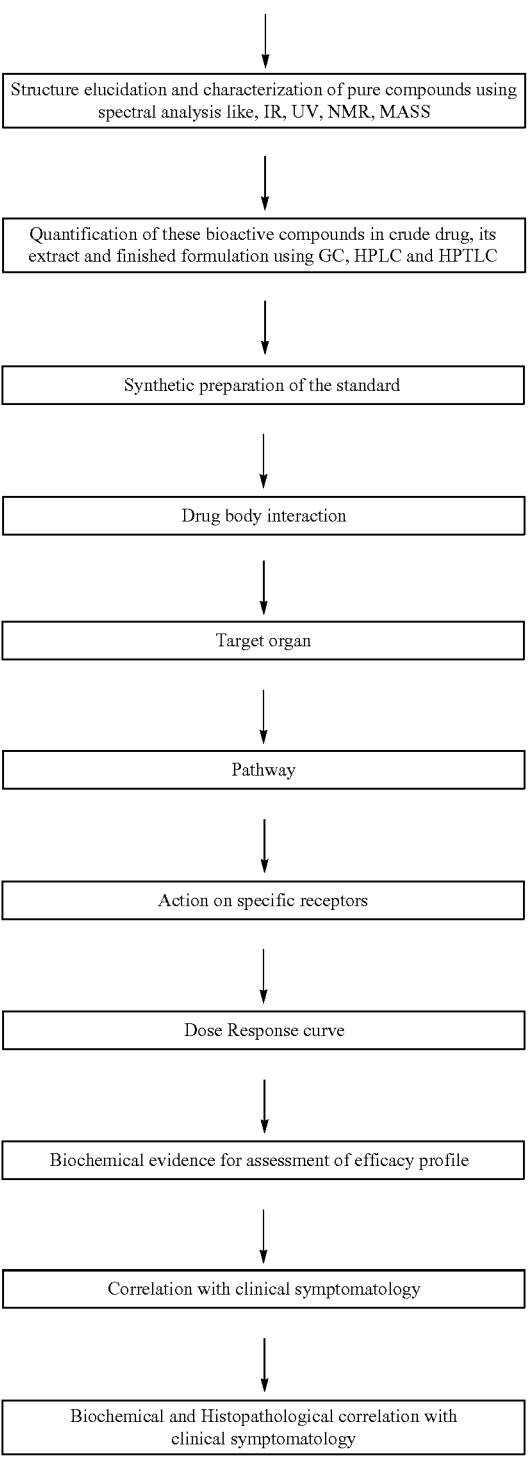

Preferably the aforesaid plants are present in the following doses—

| Name of the plant | Dose |
| --- | --- |
| 1. *Commiphora mukul* | 150-250 mg/day |
| 2. *Terminalia arjuna* | 100-250 mg/day |
| 3. *Inula recemosa* | 100-250 mg/day |
| 4. *Hippophae rhamnoides* | 200-350 mg/day |

The formulation may also comprise known additives such as minerals, vitamin, salts filter (for capsulation or to prepare syrup) and binders if required to present in trace amount.

Thus any known additives or supplement is added to prepare the final formulation if required and present in trace amount. Reference is made here in capsule form. However, it would be apparent that the preparation may also be in the form of syrup/tablet.

| Name of plant | Dose |
| --- | --- |
| *Commiphora mukul* | 200 mg/day |
| *Terminalia arjuna* | 250 mg/day |
| *Inula recemosa* | 150 mg/day |
| *Hippophae rhamnoides* | 300 mg/day |

Hypothesis:

The present novel formulation is based on the combined effect of four plant extract namely—*Commiphora mukul, Terminalia arjuna, Inula recemosa, Hippophae rhamnoides*. This formulation has been proven for its anti-atherogenic property. This effect is mediated through its binding ability to anti-inflammatory markers like TNF-α, IL-6, hs CRP. The above four drugs if prepared in specific dose enhances the level of adiponectin a known adipokines which slow down the progression of atherosclerotic process. Till date no report is available to show the role of any plant which can prevent atherosclerotic process by increasing the level of adiponectin.

Since the last decade evidences are accumulated regarding the role of adipose tissue as an endocrine organ and secretion of adipokines i.e. leptin, adiponetin, resistin, visfatin that act on non-adipose tissues such as heart, diverse cellular and whole animal function including alteration in fat metabolism and cell growth. Obesity affects the secretion of adipokines particularly increasing leptin and decreasing adiponeclin which affects heart and vascular system. In the present study the Ayurvedic test formulation treatment demonstrated increase in adiponectin level which is associated with an decrease in the risk of mortality due to CHD, as increase in adiponectin has been suggested to produce its protective effect via activation of cyclo-oxygenase-2 (COX-2) in cardiac myocytes, as inhibition of this enzyme partially reversed the cardio-protective effects of adiponectin. Adiponectin also exert anti-ischaemic effects by increasing endotheial nitric oxide. It is hypothesized that the test formulation acts through stimulation of endothelial nitric oxide by an AMP activated protein kinase (AMPK) dependent mechanism and thus have a favorable impact on micro-vascular functions.

The investigation between plasma, leptin, blood pressure and body mass index has been described. Various studies have shown that leptin may reduce blood pressure through interaction with nitric oxide pathway.

Claim slow down the atherosclerotic process by increasing adiponectin level which is evident from experimental study as well as in limited human clinical trails.

According to this invention there is provided a herbal formulation for the prevention and management of coronary heart disease comprising of the following four ingredients given as below preferably all the four—

1. *Commiphora mukul*
2. *Inula recemosa*
3. *Hippophae rhamnoides*

About the Plant:
1. *Commiphora mukul*: it belongs to Burseraceae family commonly known as Guggulu is a highly valued botanical medicine used in Ayurveda. *Commiphora mukul* tree is a small, thorny plant distributed through out of India. Guggulu and gum guggulu are the names given to a yellowish resin produced by the stem of the plant. Ketone fraction that is extracted from the resin contains the most potent cholesterol lowering components. This is composed of $C_{21}$ or $C_{27}$ steroids, with the major components being Z- & E-guggulu sterone. Guggulu contains resin, volatile oils and gum. The extract isolates ketonic steroid compounds known as guggul sterones. These compounds have been shown to provide the lipid-lowering actions. Guggulu significantly lowers serum triglycerides and cholesterol as well as LDL and VLDL cholesterol, inhibits platelet aggregation, and may increase thermogenesis through stimulation of the thyroid potentially resulting in weight loss. A direct anti-inflammatory effect has been observed for guggulu sterons.
2. *Terminalia arjuna*: it belongs to Combretaceae family & commonly known as Arjuna. It is a deciduous tree found through out India, growing to height of 60-90 feet. The active constituents to *Terminalia arjuna* include tannins, triterpenoid saponins: Arjunic acid, Arjunolic acid, oleanolic acid, Arjungenin, Arjunin, Flavonoids: Arjuolone, Arjunone, Leuteolin, Steroids: B-Sitosterol and inorganic compounds.

In Ayurveda Terminalia arjuna has been prescribed as cardio protective drug indicating its anti-atherosclerotic property. Several experimental and clinical evidence have proven the anti-atherosclerotic property of arjuna therapy reducing the incidence of atherosclerosis and the associated cardiovascular complications.

In an experimental study, a combined formulation in which Arjuna was an active ingredient, was investigated to test its effect in the regulation of cardiovascular function. The drug was found to be effective to regulate both the heart rate and arterial pressure.

Among the experimental animals this plant has proven the cardiovascular and cardiotonic property. It can be beneficial in the treatment of coronary artery disease, heart failure and possibly hyper cholesterolemia.

3. *Inula recemosa*: It belongs to composite family commonly known as Pushkarmoola. It is found in Western Himalayas. Root powder is used for medicinal purpose. At least four sesquiterpene lactones have been isolated form *Inula*. Along with other ingredients like Alantolactone, Isoalantolactone, Dihydro-alantolaction, Beta sitositosterol, Doucosterol, Inunolide account for the healing medicinal properties of this herb. Pushkarmoola is a beneficial for cardiovascular system, angina & dyspnea. Inula is known for its lipid-lowering qualities and also showed improvement in the ECG.

4. *Hippophae rhamnoides*: *Hippophae rhamnoides* belong to the Elaeagnaceae family. It grows on hills and hill sides in valleys and river beds, along sea coasts and island. *Hippophae rhamnoides* berries are most nutritious and vitamin rich fruits found in plant kingdom. *Hippophae rhamnoides* is also rich in flavonoid (vitamin p) and contains water and fat soluble vitamins. Amiono acid and different flavonids quereetin, folic acid, fatty acids, phytosterols, alpha tocopherol and phenolic compounds have been found in *Hippophae rhamnoides* fruits. The fruit, seeds and leaves contains an array of anti-oxidant compound. The leaves are equally rich source of important antioxidants including beta carotene vitamin E, Flavonoids etc. Alcoholic extract of leaves and fruits have shown anti-oxidant and immunomodulatory property.

Several recent studies indicated that *Hippophae rhamnoides* contains biologically active substance, which enhance immunity and reduces the cardiovascular over reactivity. The therapeutic efficacy of this plant exerted beneficial effect in age related deterioration of cognitive function through its anti inflammatory and anti-anxiety properties.

Research in the late 1950's and early 1960's reported that 5-Hydroxytryptamine (5-HT) have been isolated from *Hippophae rhamnoides* bark inhibited tumor growth. Several studies have shown the anti-inflammatory, anti-anxiety properties and it has capacity to improve overall mental performance particularly memory and attention span. *Hippophae rhamnoides* has potentiality to enhance the adaptability towards stress and also enhances immunity and general body resistance.

Example-I

When the hydro-alcoholic extract of *Commiphora mukul* in the dose of 20-40 mg/kg/day and *Terminalia arjuna* in the dose of 25-45 mg/kg/day was given along with high cholesterol diet to the albino rats for 3 months showed significant hypolipidemic effects. TC, HDL-c and triglyceride levels decreased and the good cholesterol HDL-c enhanced following treatment significantly. The formulation is cardio-protective due to its anti-atherogenic property.

Example-II

When the hydro-alcoholic extract of *Inula recemosa* in the dose of 30-50 mg/kg/day and *Hippophae rhamnoides* in the dose of 25-45 mg/kg/day was orally administered to high cholesterol diet induced animals showed reduction in endothelin level along with reduced arterial thickening caused due to atherosclerotic process. The inflammatory markers CRP and IL-6 decreased significantly following treatment.

Example-III

In clinical study when the hydro-alcoholic extract of *Commiphora mukul* (250-350 mg/day) and *Terminalia arjuna* (250-450) mg/day) showed beneficial role in reducing total cholesterol LDL-c and Triglycerides among cases showing abnormal lipid profile. A moderate increase in HDL-c level were also noticed. Simultaneously the Apolipo B and lipoprotein (a) also decreased following treatment indicating the anti-atherosclerosis property.

Example-IV

When the hydro-alcoholic extract of *Inula recemosa* (150-300 mg/day), *Commiphora mukul* (150-250 mg/day) and *Terminalia arjuna* (150-300 mg/day) given to subjects showing high body mass index, a significant reduction in obesity index were noticed. Similarly the triceps, sub-scapulation skin fold thickness also reduced in obese cases susceptible for an adverse cardiac event. Thus the anti-obesity role of test drug is established.

Example-V

When the organic extract of *Terminalia arjuna* (200-350 mg/day), *Hippophae rhamnoides* (200-350 mg/day) and

*Inula recemosa* (150-250 mg/day) given to cases showing high glycemic index with elevated bio-inflammatory markers, a marked reduction in CRP, IL-6 and TNF-α were noticed with a good glycemic control.

Example-VI

When the extract of *Hippophae rhamnoides* (300-450 mg/day), *Inula recemosa* (200-450 mg/day) given to the cases showing elevated homocysteine level, of reduced significantly after 3 months of treatment. As pointed out hyper Hcy is independently responsible test neurodegeneration and cardiovascular disorders this combination is neuromodulatory as well as cardio-protective.

Example-VII

The organic extract of *Commiphora mukul* (200-350 mg/day), *Terminalia arjuna* (250-350 mg/day), *Inula recemosa* (150-250 mg/day) given to subjects showing elevated leptin level with decreased adiponectin level, a significant decrease in leptin and elevation in adiponectin estimations were reduced.

Example-VIII

The organic extract of *Terminalia arjuna* (200-250 mg/day) and *Hippophae rhamnoides* (350-450 mg/day) given to cases with dyslipidemia and obesity exerted beneficial effects on oxidant injury parameters like lipid peroxidase, catalase, superoxide dysmutase, glutathione activity etc. this formulation established the anti-oxidant role of the drug. The formulation also exerted immunomodulatory effects.

Example-IX

When the hydro-alcoholic extract of *Hippophae rhamnoides* (300-450 mg/day). *Inula recemosa* (250-350 mg/day) and *Terminalia arjuna* (200-300 mg/day) given to subjects showing high blood pressure with high anxiety or depression levels, a reduction in both systolic and diastolic blood pressure along with reduction in anxiety level were observed.

Example-X

When the hydro-alcoholic extract of *Commiphora mukul* (150-250 mg/day), *Terminalia arjuna* (200-350 mg/day), *Inula recemosa* (100-250 mg/day) and *Hippophae rhamnoides* (200-350 mg/day) was administered to cases showing involvement with various CHD risk factors exerted better results. The test drug exerted hypolipidaemic, anti-obesity, anti-atherogenic, anti-oxidant, anti-anxiety with hmocysteine reducing property. The test drug has a potent effecting in improving the endothelial dysfunction, thus it is proposed to be a potent remedial measure for the prevention/minimizing the adverse cardiac event.

It is to be noted that the present invention is susceptible to modifications, adaptations and changes by those skilled in the art Such variant embodiments employing the concepts and features of this invention are intended to be within the scope of the present invention.

We claim:

1. A composition for treating coronary heart disease consisting essentially of therapeutically effective amounts of *Commiphora mukul* extract, *Terminalia arjuna* extract, *Inula recemose* extract, and *Hippophae rhamonoides* extract.

2. The composition as claimed in claim 1, wherein said *Commiphora mukul* extract is present in an amount of 150-250 mg, said *Terminalia arjuna* extract is present in an amount of 100-250 mg, said *Inula recemose* extract is present in an amount of 100-250 mg, and said *Hippophae rhamonoides* extract is present in an amount of 200-350 mg.

3. A method of preparing the composition of claim 1 consisting essentially of preparing a hydro-alcoholic plant extract consisting essentially of *Commiphora mukul* extract, *Terminalia arjuna* extract, *Inula recemose* extract, and *Hippophae rhamonoides* extract by placing *Commiphora mukul, Terminalia arjuna, Inula recemose,* and *Hippophae rhamonoides* in a solution of water and methanol at 70°-80° C. and maintaining the pH of the solution between 7-10 to yield said extracts.

4. The method as claimed in claim 3, wherein said *Commiphora mukul* extract is present in an amount of 150-250 mg, said *Terminalia arjuna* extract is present in an amount of 100-250 mg, said *Inula recemose* extract is present in an amount of 100-250 mg, and said *Hippophae rhamonoides* extract is present in an amount of 200-350 mg.

5. The method as claimed in claim 3, wherein water and methanol are present in a ratio of 70:30, respectively.

6. A composition for treating coronary heart disease consisting essentially of therapeutically effective amounts of *Commiphora mukul* extract, *Terminalia arjuna* extract, *Inula recemose* extract, *Hippophae rhamonoides* extract and at least one additive selected from the group consisting of minerals, vitamins, and salts.

* * * * *

UNITED STATES PATENT AND TRADEMARK OFFICE
CERTIFICATE OF CORRECTION

PATENT NO. : 8,318,216 B2
APPLICATION NO. : 12/866389
DATED : November 27, 2012
INVENTOR(S) : GoVind Prasad Dubey et al.

It is certified that error appears in the above-identified patent and that said Letters Patent is hereby corrected as shown below:

In the Claims

Column 10, Lines 17-18, Claim 1, delete "Inula recemosa" and insert -- Inula racemosa --

Column 10, Line 18, Claim 1, delete "Hippophae rhamonoides" and insert
-- Hippophae rhamnoides --

Column 10, Line 22, Claim 2, delete "Inula recemosa" and insert -- Inula racemosa --

Column 10, Lines 23-24, Claim 2, delete "Hippophae rhamonoides" and insert
-- Hippophae rhamnoides --

Column 10, Line 28, Claim 3, delete "Inula recemosa" and insert -- Inula racemosa --

Column 10, Lines 28-29, Claim 3, delete "Hippophae rhamonoides" and insert
-- Hippophae rhamnoides --

Column 10, Line 30, Claim 3, delete "Inula recemosa" and insert -- Inula racemosa --

Column 10, Lines 30-31, Claim 3, delete "Hippophae rhamonoides" and insert
-- Hippophae rhamnoides --

Column 10, Line 37, Claim 4, delete "Inula recemosa" and insert -- Inula racemosa --

Column 10, Line 38, Claim 4, delete "Hippophae rhamonoides" and insert
-- Hippophae rhamnoides --

Column 10, Lines 44-45, Claim 6, delete "Inula recemosa" and insert -- Inula racemosa --

Signed and Sealed this
Sixteenth Day of April, 2013

Teresa Stanek Rea
*Acting Director of the United States Patent and Trademark Office*

CERTIFICATE OF CORRECTION (continued)
U.S. Pat. No. 8,318,216 B2

Column 10, Line 45, Claim 6, delete "Hippophae rhamonoides" and insert
-- Hippophae rhamnoides --